(12) United States Patent
Blümich et al.

(10) Patent No.: US 8,952,691 B2
(45) Date of Patent: Feb. 10, 2015

(54) MAGNETIC RESONANCE USING A PHASE-MODULATED PULSE TRAIN WITH A CONSTANT SMALL FLIP ANGLE, CAUSING A CONSTANT IN POWER WALSH TRANSFORM OF THE PULSE TRAIN SEQUENCE OF PHASES

(75) Inventors: Bernhard Blümich, Rott (DE); Marcus Greferath, Dublin (IE); Eimear Byrne, Crumun (IE); Qingxia Gong, Aachen (DE)

(73) Assignees: RWTH Aachen, Aachen (DE); University College Dublin, National University of Ireland, Dublin (IE)

( * ) Notice: Subject to any disclaimer, the term of this patent is extended or adjusted under 35 U.S.C. 154(b) by 914 days.

(21) Appl. No.: 13/124,339

(22) PCT Filed: Oct. 8, 2009

(86) PCT No.: PCT/EP2009/063124
§ 371 (c)(1),
(2), (4) Date: Jun. 21, 2011

(87) PCT Pub. No.: WO2010/043548
PCT Pub. Date: Apr. 22, 2010

(65) Prior Publication Data
US 2011/0241667 A1    Oct. 6, 2011

(30) Foreign Application Priority Data

Oct. 16, 2008 (EP) .................................. 08105593

(51) Int. Cl.
*G01N 24/08* (2006.01)
*G01N 24/10* (2006.01)
(Continued)

(52) U.S. Cl.
CPC .............. *G01N 24/08* (2013.01); *G01N 24/087* (2013.01); *G01N 24/10* (2013.01); *G01R 33/44* (2013.01);
(Continued)

(58) Field of Classification Search
USPC ........................ 324/300–322; 600/407–435; 382/128–131; 424/9.33
See application file for complete search history.

(56) References Cited

U.S. PATENT DOCUMENTS 3,475,680 A * 10/1969 Anderson et al. ............. 324/312
3,530,373 A *  9/1970 Waugh ........................... 324/311
(Continued)

FOREIGN PATENT DOCUMENTS

EP           2177925 A1 *  4/2010
WO   WO 2010043548 A1 *  4/2010

OTHER PUBLICATIONS

Mastikhin, I.V., "Rapid determination of the RF pulse flip angle and spin-lattice relaxation time for materials imaging," Journal of Magnetic Resonance, Academic Press, Orlando, FL, US, vol. 172, No. 2, Feb. 1, 2005, pp. 231-237, XP004707335, IISSN: 1090-7807.
(Continued)

*Primary Examiner* — Melissa Koval
*Assistant Examiner* — Tiffany Fetzner
(74) *Attorney, Agent, or Firm* — BainwoodHuang

(57) ABSTRACT

A method for performing magnetic resonance measurements on a sample includes applying a first predetermined number of pulse trains for excitation, each pulse train having a constant amplitude and including a second predetermined number of pulses spaced by a predetermined time interval. The pulse trains are modulated by a bent function. After each pulse, data is sampled. Preferably a square number of pulses is generated being constant in power, and the Walsh transform of the sequence of their phases is constant in power, so that the power of the excitation in time and frequency domain is constant. The method can reduce power requirements and may permit undercutting specific absorption rate (SAR) limits due to the small excitation power necessary to create time signals with reasonable signal to noise ratio.

15 Claims, 5 Drawing Sheets

(51) Int. Cl.
*G01R 33/44* (2006.01)
*G01R 33/561* (2006.01)
*G01R 33/60* (2006.01)
*G01R 33/46* (2006.01)

(52) U.S. Cl.
CPC .......... *G01R 33/4616* (2013.01); *G01R 33/561* (2013.01); *G01N 24/081* (2013.01); *G01N 24/084* (2013.01); *G01R 33/441* (2013.01); *G01R 33/60* (2013.01)
USPC ............................ 324/307; 324/303; 324/316

(56) References Cited

U.S. PATENT DOCUMENTS

| | | | | |
|---|---|---|---|---|
| 3,530,374 A * | 9/1970 | Waugh et al. | ................. | 324/311 |
| 4,065,714 A * | 12/1977 | Hill | ................. | 324/314 |
| 4,639,671 A * | 1/1987 | Macovski | ................. | 324/309 |
| 4,656,425 A * | 4/1987 | Bendel | ................. | 324/309 |
| 4,678,996 A * | 7/1987 | Haacke et al. | ................. | 324/309 |
| 5,431,901 A * | 7/1995 | Halpern et al. | ................. | 424/9.33 |
| 5,608,321 A | 3/1997 | Garroway et al. | | |
| 5,631,561 A * | 5/1997 | Stetter | ................. | 324/322 |
| 6,127,824 A * | 10/2000 | Smith et al. | ................. | 324/300 |
| 6,392,408 B1 * | 5/2002 | Barrall et al. | ................. | 324/300 |
| 6,472,870 B1 * | 10/2002 | Bendall et al. | ................. | 324/307 |
| 6,489,767 B1 * | 12/2002 | Prado et al. | ................. | 324/318 |
| 6,597,170 B1 * | 7/2003 | Beard et al. | ................. | 324/303 |
| RE43,264 E * | 3/2012 | Walsh | ................. | 324/303 |
| 2004/0032258 A1 | 2/2004 | Blümich | | |
| 2008/0174309 A1* | 7/2008 | Pusiol et al. | ................. | 324/306 |
| 2011/0241667 A1* | 10/2011 | Blumich et al. | ................. | 324/303 |

OTHER PUBLICATIONS

Heid, O., "Burst Excitation Pulses," Magnetic Resonance in Medicine, Academic Press, Duluth, MN, US, vol. 38, No. 4, Oct. 1, 1997, pp. 585-590, XP000720009, ISSN: 0740-3194.

Zha, L., et al., "Optimized Ultra-Fast Imaging Sequence (OUFIS)," Magnetic Resonance in Medicine, Academic Press, Duluth, MN, US, vol. 33, No. 3, Mar. 1, 1995, pp. 377-395, XP000494898, ISSN: 0740-3194.

* cited by examiner

MAGNETIC RESONANCE USING A PHASE-MODULATED PULSE TRAIN WITH A CONSTANT SMALL FLIP ANGLE, CAUSING A CONSTANT IN POWER WALSH TRANSFORM OF THE PULSE TRAIN SEQUENCE OF PHASES

BACKGROUND

The invention relates to performing magnetic resonance measurements such as spectroscopic NMR (nuclear magnetic resonance) measurements as well as in MRI (magnetic resonance imaging).

In NMR experiments spins in a sample are aligned by a static magnetic field. The aligned spins are then excited by applying electromagnetic pulses to the sample. This can be done in immobile spectrometers which often comprise a superconducting magnet or with portable NMR devices which are e.g. known by the trademark NMR-Mouse in the market. In particular when imaging human beings it is important to limit the excitation power which is introduced by the electromagnetic pulses to the patient for to undercut specific absorption rate (SAR) limits. Furthermore, when performing NMR measurements with mobile NMR devices it is necessary to limit excitation power to increase battery life. Therefore, low excitation power is desirable. Nevertheless, in NMR techniques known from prior art the drawback of low excitation power is an insufficient response peak power which results in a low signal to noise ratio and necessitates to repeat the measurements frequently while summing up the results to increase signal to noise. Similar problems arise in other magnetic resonance methods as electron spin resonance (ESR) and nuclear quadrupole resonance (NQR).

SUMMARY

It is desired to solve the problems known from prior art at least partly and in particular to provide a method for performing magnetic resonance measurements and a respective apparatus to allow measurements with a good signal to noise ratio at low excitation peak power and high response peak power.

According to a disclosed method, magnetic resonance measurements are performed on a sample, in which a first predetermined number of pulse trains each comprising a second predetermined number of pulses spaced by a predetermined time interval are applied for excitation, each pulse having a constant amplitude. The pulse trains are modulated by a bent function (known in this context as Frank sequences as well), wherein after each pulse data is sampled.

It is understood that the term magnetic resonance measurements covers at least Nuclear Magnetic Resonance (NMR) measurements, Nuclear Quadrupole Resonance (NQR) measurements, and Electron Spin Resonance (ESR) measurements. The term "the pulse trains are modulated by a bent function" is preferably understood such that a predetermined square number $m^2$ of pulses are generated which form the first predetermined number of pulse trains. These pulse trains are constant in power, and the Walsh transform of the sequence of their phases is constant in power, too. This means that the spectral power density of the sequence is constant. The term amplitude is understood as the sum of the squares of the real and imaginary components of the pulse trains in the rotating coordinate frame representation.

It is preferred to chose a positive natural number m, and a sequence of numbers $z(n)$, $n=0, \ldots, m^2-1$ is generated such that all $z(n)$ have values ranging between $0, 1, \ldots, m-1$.

The sequence of these numbers has the additional property that its Walsh transform, i.e. the sequence $Z(N)$ defined as $$Z(N) := \sum_{n=0}^{m^2-1} \exp\left(\frac{2\pi i}{m} z(n)\right) \exp\left(-\frac{2\pi i}{m^2} nN\right)$$

for $N=0, \ldots, m^2-1$ has constant absolute value. Sequences that exhibit this property are called bent functions in this context. The term i denotes the imaginary unit, which means that the square of i equals $-1$.

One example for the pulse trains is given by $z(n) := n_1 n_0$, where $n = m n_1 + n_0$ which are the unique natural numbers in the range $0, \ldots, m-1$ that allow the m-ary representation of $n=0, \ldots, m^2-1$.

$z(n)$ as defined above can be varied e.g. in at least one of the following ways:
(a) $z_1 = z(n) + a$, where a is an arbitrary number in $0, \ldots, m-1$;
(b) $z_2 = z(n+a)$, where a an arbitrary number in $0, \ldots, m^2-1$;
(c) $z_3 = z(n \cdot b)$, where b is a number between $0, \ldots, m^2-1$ such that the greatest common divisor of b and m is 1; and
(d) $z_4 = z(n) \cdot b$, where b is a number between $0, \ldots, m-1$ such that the greatest common divisor of b and m is one.

It is to be understood that it is possible to combine the possibilities (a) to (d) in such way that the function z in any of the possibilities (a) to (d) can be replaced by any the function $z_1$, $z_2$, $z_3$ and $z_4$.

For the NMR measurement a sequence of $m^2$ pulses is generated from z in the following way: all pulses have the same and preferably very small flip angle $\theta$ and the pulse direction, i.e. the angle between the pulse axis and the x-axis is given by $$\phi(n) = \frac{2\pi}{m} z(n), \text{ for } n = 0, \ldots, m^2 - 1.$$

Using this pulse sequence for an NMR measurement allows for a homogeneous excitation of the frequencies within a frequency window determined by the pulse spacing in the time domain. This leads to the possibility to use low excitation power while having maximum response power and thus a good signal to noise ratio. Data acquisition is preferably done after each pulse applied to the probe.

Other bent functions of length $m^2$ could be used for NMR measurements with the same benefit. An example for such a bent function comes from the mathematical theory of Gaussian sums and is given by the sequence $z(n) = n^2$, $n = 0, \ldots, m^2 - 1$.

Likewise, a sequence of pulse trains with constant small flip angle $\theta$ is generated where $$\phi(n) = \frac{2\pi}{m^2} z(n), \text{ for } n = 0, \ldots, m^2 - 1.$$

Therefore, the partition of pulse phases that this function generates is finer than that of the example given above.

The fact that the Walsh transform of all these functions is constant in absolute value implies that all frequencies in the frequency domain are covered with equal intensity, particularly also the 0 frequency. This allows scanning a time grid wherein adjacent points are separated by the time interval.

In one embodiment the bent function may be chosen such that the pulse trains comprise a series of the first predetermined number $n_1$ of wavelet functions, where each pulse train is defined by the second predetermined number $n_0$ of discrete points in time.

Preferably the ranges m of the first number $n_1$ and the second number $n_0$ are identical. This results in one important example of bent functions that can be understood as wavelets in terms of discrete representations of rotating waves $$x(t)=\exp\{i2\pi ft\} \quad (1)$$

over finite durations of time t and having a frequency f. The term i denotes the imaginary unit, whereas the square of i is −1. In a discrete representation the frequencies f can be written as $$f=n_1/(m\Delta t) \quad (2)$$

where m is an integer, $\Delta t$ is the predetermined time interval, and $n_1$ is a counter value. The time t is an integer multiple of the predetermined time interval:

$$t=n_0\Delta t \quad (3)$$

If x(t) is understood as a discrete representation of a rotating wave then the integer $n_1$ counts the number of turns of the wave within a fixed time (m $\Delta t$) whereas the integer $n_0$ counts the time increments within a rotating wave of given frequency f.

This means the pulse trains can be described as $$x(n\Delta t)=\exp\{i2\pi n_1 n_0/m\}. \quad (4)$$

with $$n=mn_1+n_0.$$

For $$0 \leq n_1 \leq m-1 \text{ and } 0 \leq n_0 \leq m-1$$

the largest values of the first and the second number are both m so that the pulse trains are m wavelets each defined at m successive values of $n_0$ As the absolute value of x is always one, and the envelope of the wavelets is rectangular. A Fourier transformation of the pulse trains reveals that the resulting power spectrum is constant.

Therefore, a homogeneous excitation of the frequencies within the frequency window may be possible. Therefore, by exciting the spins with a multitude of constant-amplitude, small flip angle pulses the phases of which are discrete approximations of helices constituting complex wavelets defined on a discrete time grid, it is possible to use minimum excitation power while having maximum response power and thus a good signal to noise ratio. Due to the intermittent excitation and sampling of data without longer delays for to await relaxation phenomena, fast data sampling is possible. In this context it is preferred to sample one data point after each pulse.

The use of wavelet functions, in particular as described above, has been found to be advantageous as it is possible to measure results with sufficient resolution with reasonable limitations on the hardware used to generate the pulse trains and sample the respective data. In particular, constant amplitude radio frequency (rf) pulse trains can be generated with simple nonlinear electronic components including rf amplifiers, while the pulse phase can easily be set with high accuracy using modern rf electronics.

The spectrum of excitation frequencies may cover zero and integer multiples of a frequency interval.

This allows a well-defined coverage of the frequency domain. The frequency interval of one wavelet is the reciprocal value of the product of the predetermined number of pulse trains and the predetermined time interval.

The time interval may be determined such that by each pulse the net magnetization of the sample is rotated by a small flip angle.

It is understood that the term small flip angle covers flip angles of less than 0.5°, in particular less than 0.2°, in particular less than 0.1° or less than 0.01° or even less than 0.005°. The rotation of the net magnetization by a small flip angle allows the rapid sampling of data points.

The method may allow for rapid sampling of spectra and/or of imaging data if a respective magnetic field gradient is present with low excitation power and good signal to noise ratio.

A An apparatus for executing the disclosed method may include:

a) a magnet arrangement for creating a static magnetic field in a sample;
b) a coil for exciting, refocusing and sampling a spin signal in the sample, and
c) a controller that causes the magnet arrangement and coil to apply the pulse trains as described above to the sample.

According to an improvement the magnet arrangement comprises at least one magnet of at least one of the following kinds of magnets:

a) a superconducting magnet;
b) a permanent magnet; and
c) an electromagnet.

The apparatus and the method can be used in low-field NMR spectroscopy with NMR frequencies of 5 MHz or more, e.g. 10 MHz and more and in high-field NMR spectroscopy and imaging with NMR frequencies of hydrogen of 300 MHz (Megahertz) and more, in particular of 600 MHz and more. In particular in imaging measurements in static magnetic fields of 3 Tesla and more, in particular of 7 T and more, and in particular 11 T and more, it may be possible to undercut specific absorption rate (SAR) limits with reasonable signal to noise ratios. Therefore, high resolution imaging in particular of human beings is possible.

According to a further improvement the magnet arrangement is a single-sided magnet arrangement.

It is preferred that these single-sided magnet arrangements have a sufficiently homogeneous stray field, so that an impulse response can be observed in the form of a free induction decay.

According to a further improvement the magnet arrangement is a small permanent magnet arrangement with a sufficiently homogeneous field in the bore. It is understood that a small permanent magnet arrangement has a diameter of at most 30 cm (centimeters), preferably at most 20 cm, in particular at most 10 cm or even at most 5 cm or 3 cm.

The method and apparatus may allow the measurement of spectra with reasonable signal to noise ratio with an excitation power significantly lower than that of the pulse sequences known in the art of Fourier NMR. Therefore, in particular movable NMR tools or devices can be used with a reasonably low consumption of electric energy. Compared to prior art pulse sequences the method and apparatus may enable the reduction of the excitation power by a factor of at least the order of four and thus a reduction of the energy consumption by a factor of at least the order of two with comparable results. This allows a significant reduction of battery capacities needed for movable NMR tools. Furthermore, the excitation power is reduced. This is particularly important for NMR tools used in bio-sensing applications, in sensing and control of chemical processes, in bore-hole applications, in airport security applications such as NMR fluid screening and NQR explosives and drug detection, in conducting NMR at contaminated sites like e.g. in nuclear contaminated environments or the like, in single-sided NMR of large or precious objects, and in NMR imaging in an emergency vehicle. One preferred application is in bore-hole NMR e.g. analyzing fluids in porous rocks. In these cases the measurements are performed with mobile instrumentation underground and the energy supply is critical.

With the method and apparatus it may be possible to provide NMR tools having a button cell as an energy source instead of the large and heavy battery packs currently required.

According to a further improvement the apparatus comprises means for generating magnetic field gradients for spatially resolved sampling of NMR signals.

The means for generating magnetic field gradients can preferably comprise one or more gradient coils which are designed to create defined magnetic gradient fields at least at the sensitive volume of the probe where the coil and the sample are situated. The term sample is understood to comprise the material which is to be measured and can e.g. be a liquid sample in a container, i.e. e.g. a glass tube or the like, a human body or a part of it and so forth.

The method and apparatus can be used e.g. in NMR, NQR, MRI, and ESR measurements. One use for the NQR detection is to detect the presence of explosives and/or narcotics. The disclosed method and apparatus may also be used for bore-hole NMR measurements, well-logging measurements, and/or measurements below the earth surface in porous environments comprising fluids. The term "wells" is understood to include water and/or oil wells. The term "fluid" is understood to include gases and/or liquids.

BRIEF DESCRIPTION OF THE DRAWING

Embodiments will now be described in detail by way of example only with reference to the accompanying drawings, in which the following is depicted schematically.

DETAILED DESCRIPTION

Figure 1:
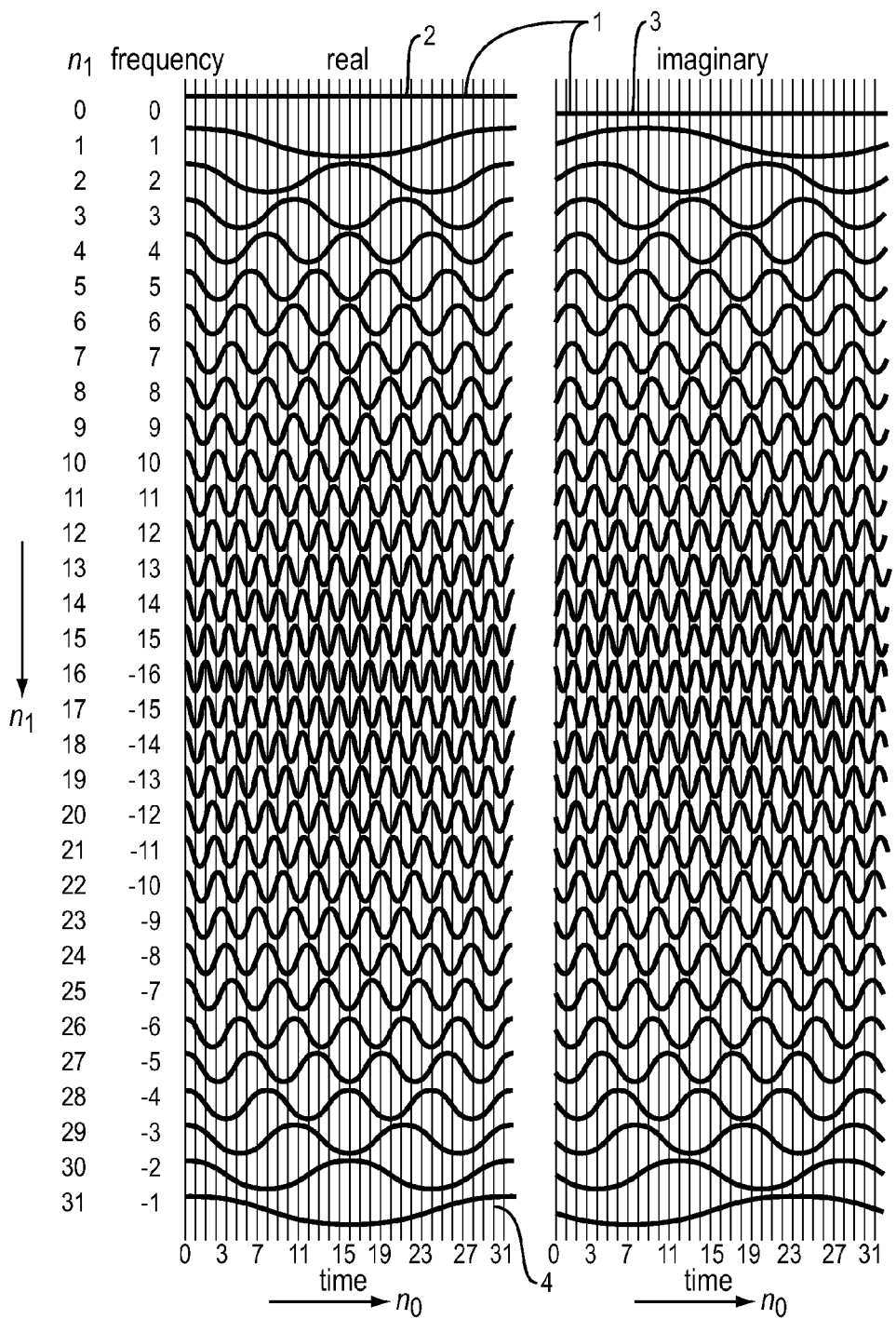
FIG. 1 an embodiment of an NMR pulse sequence.

FIG. 1 depicts schematically an NMR pulse train with 1024 data points. For the sake of clarity the pulse sequence is illustrated in FIG. 1 in a two-dimensional fashion. According to the m-ary representation of $n=mn_1+n_0$ the horizontal numerals refer to $n_0$ whereas the vertical numerals refer to $n_1$. Both range from $0, \ldots, 31$, where for typesetting reasons the $n_0$ numerals are only partly furnished.

The pulse trains 1 are shown with their respective real component 2 and the imaginary component 3 corresponding to the projections of the pulse trains 1 to the x and y directions in the rotating coordinate frame the frequency of which is defined by the so called Larmor frequency which is proportional to the static magnetic field at the sample. For sake of clarity the reference numerals are only depicted for one pulse train 1 (wavelet) with frequency $n_1=0$ but not for the respective pulse trains 1 with $n_1=1$ to 31 (according to equation (4) above). Therefore, both the first number of pulse trains 1 (wavelets) and the second number of pulses per sequence are 32. 32 time intervals 4 are depicted as being separated by vertical lines.

In each time interval 4 one pulse is applied and one data point is sampled. In one excitation scan 1024 pulses are applied successively for excitation, and hence 1024 data points are sampled. For each of the 32 values of $n_1$, pulse trains 1 in the form of wavelets according to equation (4) above are applied successively for excitation. Each pulse train 1 corresponding to one specific wavelet excites one frequency window determined by the time interval 4 in the time domain and the number m of pulse trains. Multiple pulse trains 1 are applied without a recycle delay. The pulses of all pulse trains 1 have constant amplitude defined as the sum of the squares of the respective real component 2 and the respective imaginary component 3. One data point is sampled at the end of a time interval 4. The pulse trains 1 are applied to the sample successively. First, the pulse train 1 being a pulse sequence of the respective pulses enumerated as 0 in FIG. 1 corresponding to $n_1=0$ in equation (4) is applied to the sample in time intervals with $n_0=0, \ldots, 31$. Next, the pulse train with $n_1=1, \ldots, 31$ are applied in time intervals each with $n_0=0, \ldots, 31$. In any combination of $n_1$ and $n_0$ one data point is sampled. Therefore, a total of 1024 (32 rows and 32 columns) data points is sampled.

Figure 2:
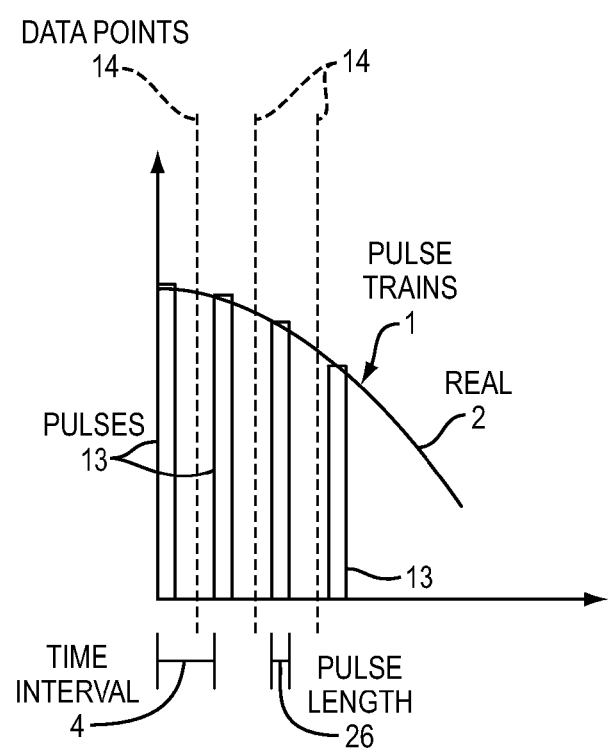
FIG. 2 an example of pulses of one pulse train.

FIG. 2 discloses a part of the pulse sequence in FIG. 1 in more detail. The real component 2 of one pulse train 1 is depicted in part. This pulse train 1 has the shape of one of the wavelets as discussed above. The pulse train 1 is split into a train of pulses 13. In each time interval 4 one pulse 13 is applied and one data point 14 is sampled. The height of the respective pulse 13 is modulated according to the value of the pulse train 1 at the respective time. Each pulse 13 has a pulse length 26 being smaller than the time interval 4.

Figure 3A:
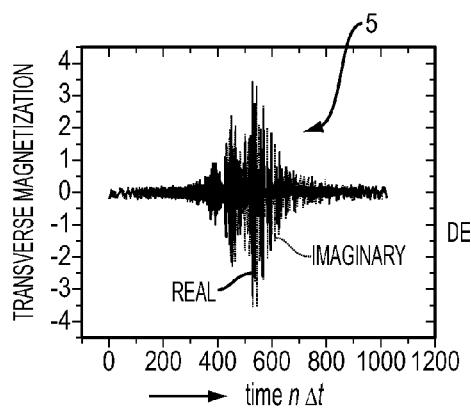
FIG. 3(a) and FIG. 3(b) an example of an NMR signal and the respective NMR spectrum respectively.
Figure 3B:
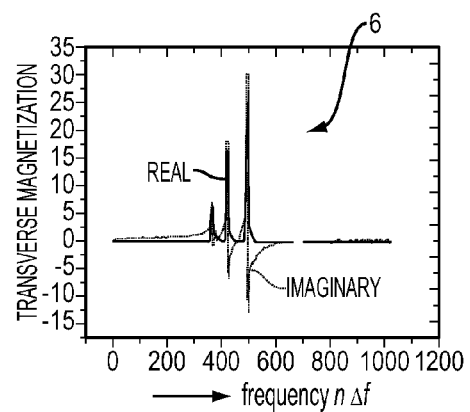

FIG. 3(a) depicts a respective time signal 5 having real and imaginary components which was measured with the pulse sequence depicted in FIG. 1. FIG. 3(a) depicts the respective spectrum 6 gathered by a Fourier transformation of the time signal 5. The spectrum 6 has a real and an imaginary component as well. Time signal 5 was measured from an ethanol sample with a 300 MHz (1H (proton) frequency) spectrometer. The excitation power was 35 µW (microwatts).

Figure 4:
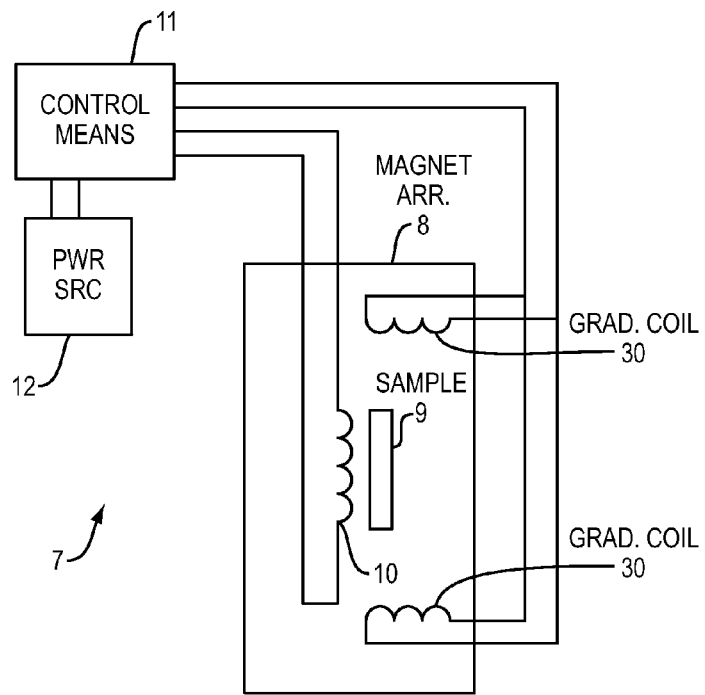
FIG. 4 an embodiment of a magnetic resonance measurement apparatus.

FIG. 4 depicts schematically an NMR apparatus 7. The apparatus 7 comprises a magnet arrangement 8 which comprises e.g. superconducting magnets, electromagnets or permanent magnets. The magnet arrangement 8 can be such that the sensitive volume in which the sample 9 is inserted is generated within the magnet arrangement 8 or on one side of the magnet arrangement 8. The magnet arrangement 8 creates a static magnetic field at the sensitive volume which has to be located inside the sample 9. The apparatus 7 further comprises a coil 10 for exciting and sampling a spin signal in the sample 9. The coil 10 can be a surface coil, a solenoid coil or any other coil that is able to generate and sample the respective magnetic fields at the position of the sample 9.

The apparatus 7 further comprises control means 11 which are e.g. included in a computer or electronic device. The control means 11 are used to generate a signal with the coil 10 at the position of the sample 9. The control means 11 are able to control the frequency, the shape and amplitude of the respective signal. Furthermore, the control means 11 are able to sample the signal received by the coil 10 after the pulses of the pulse trains 1. The coil 10 is shaped such that the sample 9 is within the so called sensitive volume of the coil 10 in the magnet arrangement 8.

The control means 11 are provided with electrical energy by a power source 12. This power source 12 comprises e.g. for mobile applications batteries. It may be possible to reduce the capacity of the batteries significantly as by the excitation with pulse trains 1 modulated by a bent function and the intermittent data sampling in between pulses 13 of the pulse trains 1 only low excitation power and thus only a small battery capacity is necessary. In high field MRI it may be possible to undercut SAR due to the small excitation power necessary to generate time signals 5 with a reasonable signal to noise ratio.

FIG. 4 also shows two gradient coils 30 controlled by the control means 11 in order to generate magnetic gradient fields and produce spatially resolved sampling of magnetic resonance measurement signals.

Figure 5:
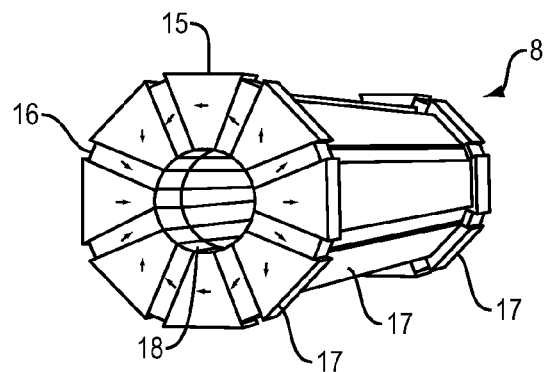
FIG. 5 a first example of a magnet arrangement which can be used in a magnetic resonance measurement apparatus.

FIG. 5 depicts schematically a first example of a magnet arrangement 8 which can be used in an apparatus 7. The magnet arrangement 8 is e.g. shaped from first magnets 15 of trapezoidal cross section and second magnets 16 of rectangular cross section. The arrows in the magnets 15, 16 depict schematically the magnetization of these magnets 15, 16.

The first magnets 15 and second magnets 16 form three ring magnets 17 aligned such that a bore 18 for the sample 9 is created. These first magnets 15 and second magnets 16 are designed and arranged such that the magnet arrangement 8 forms a Halbach configuration. This means the polarization of the first magnets 15 and second magnets 16 are arranged to generate a strong magnetic field in the bore 18 within the ring magnets 17 and a very small field outside the ring magnets 17. This magnet arrangement 8 allows the generation of highly homogeneous fields within the ring magnets 17. The second magnets 16 can be moved relatively to the second magnets 15 towards the bore 18 and away from the bore 18 to increase the homogeneity of the magnetic field within the bore 18.

Figure 6:
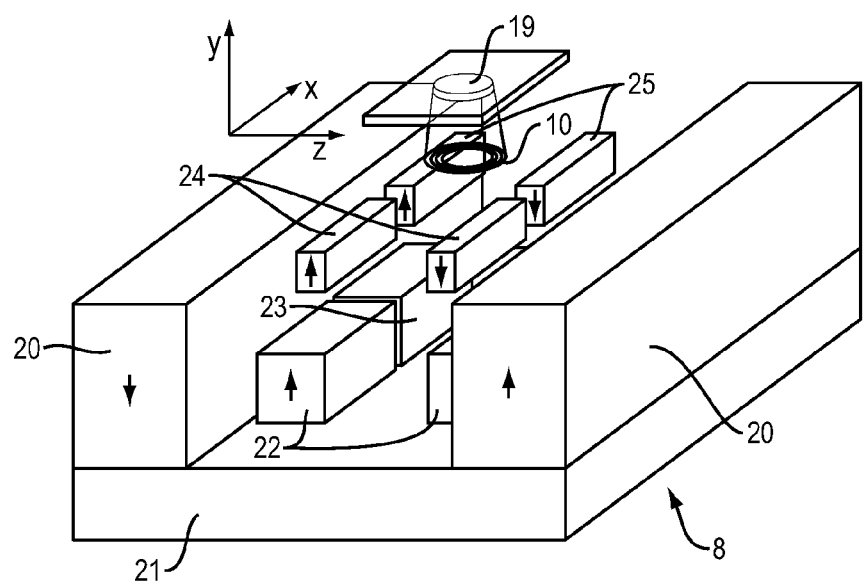
FIG. 6 a second example of a magnet arrangement which can be used in a magnetic resonance measurement apparatus.

FIG. 6 depicts a further example of a magnet arrangement 8 which can be used in an apparatus 7. The magnet arrangement 8 generates a sensitive volume 19 for single-sided NMR. In comparison to the first example of the magnet arrangement 8 as shown in FIG. 5 the sensitive volume 19 is in the second example on one side of the magnet arrangement 8 whereas the sensitive volume of the magnet arrangement 8 of FIG. 5 is within the bore 18.

The magnet arrangement 8, as depicted in FIG. 6, comprises two first permanent magnets 20 for providing a first magnetic field at the sensitive volume 19. The two first permanent magnets 20 are arranged such that their polarity is antiparallel. The two first permanent magnets 20 are arranged on an iron yoke 21 connecting the two first permanent magnets 20. Above the yoke 21 and in between the two first permanent magnets 20 the magnet arrangement 8 further comprises a first pair 22 of shim magnets, a second pair 23 of shim magnets, a third pair 24 of shim magnets and a fourth pair 25 of shim magnets. The details of how to shim the magnetic field within the sensitive volume 19 is disclosed in EP 1 944 617 A1 which is incorporated by reference.

Furthermore, an RF coil 10 for excitation and detection of signals in and from the sensitive volume 19 is further situated on the side opposite to the yoke 4. The coil 11 is in this case a surface coil.

Preferably a square number $m^2$ of pulses is generated. These pulses are constant in power, and the Walsh transform of the sequence of their phases is constant in power, too. This means that the power of the excitation in time and frequency domain is constant.

Figure 7:
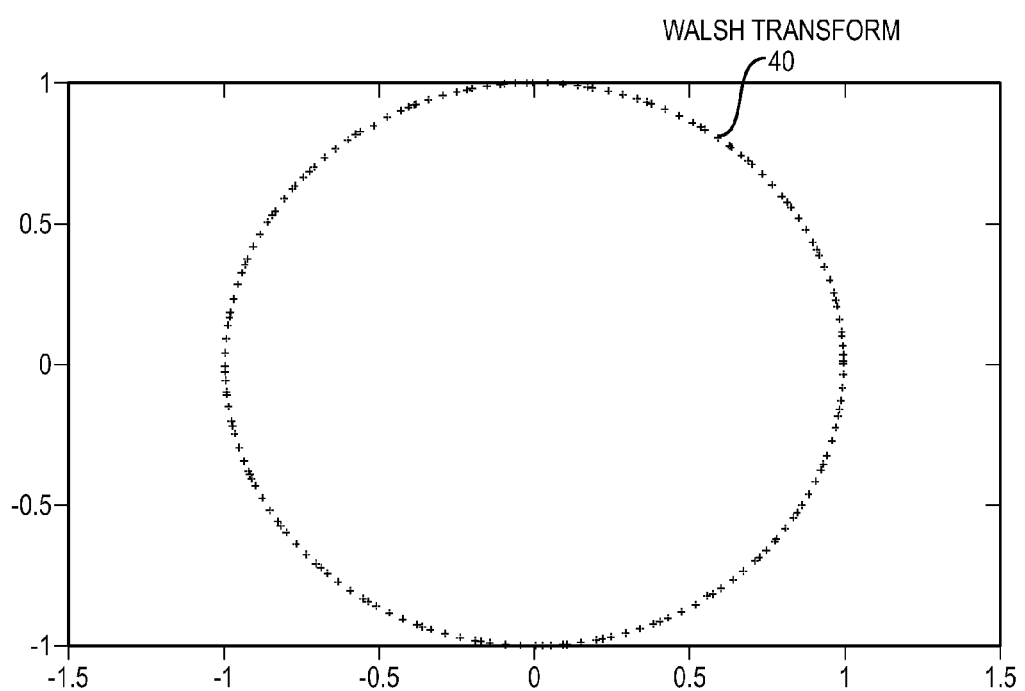
FIG. 7 a plot of a Walsh transform of the NMR pulse sequence of FIG. 1.

FIG. 7 shows a plot of a Walsh transform of the sequence of pulse trains 1 of FIG. 1. As shown, the points 40 of the Walsh transform form a unit circle in the complex plane, illustrating that a Walsh transform of a sequence of phases of each of the magnetic resonance pulse trains 1 is constant in amplitude and therefore also constant in power.

It may be possible to reduce the capacity of the power supply significantly as by the excitation with pulse trains shaped as bent functions and the intermittent data sampling in between the pulses of the pulse trains only necessitates low excitation power and thus e.g. only a small battery capacity as a power supply is necessary. In high field MRI it may be possible to undercut SAR due to the small excitation power necessary to generate time signals 5 with a reasonable signal to noise ratio.

REFERENCE NUMERALS 1 pulse train
2 real component
3 imaginary component
4 time interval
5 time signal
6 spectrum
7 NMR apparatus
8 magnet arrangement
9 sample
10 coil
11 control means
12 power source
13 pulse
14 data point
15 first magnet
16 second magnet
17 ring magnet
18 bore
19 sensitive volume
20 first permanent magnet
21 second permanent magnet
22 first pair of shim magnets
23 second pair of shim magnets
24 third pair of shim magnets
25 fourth pair of shim magnets
26 pulse length

The invention claimed is:

1. A method of operating a magnetic resonance system in order to perform magnetic resonance measurements on a sample, comprising:
    applying, by the magnetic resonance system, a first predetermined number of magnetic resonance pulse trains as a source of magnetic resonance excitation in order to generate a spectrum of excitation frequencies, each pulse train of the magnetic resonance pulse trains, having a constant amplitude and including a second predetermined number of pulses spaced by a predetermined time interval, each of the magnetic resonance pulse trains being modulated by a bent function; and
    sampling, by the magnetic resonance system, magnetic resonance data after each of the pulses of each of the magnetic resonance pulse trains,
    wherein each of the magnetic resonance pulse trains being modulated by the bent function causes:

(i) each of the magnetic resonance pulse trains to be constant in power, and (ii) a Walsh transform of the sequence of phases of each of the magnetic resonance pulse trains, to also be constant in power.

2. A method according to claim 1, wherein the bent function is chosen such that the magnetic resonance pulse trains include a series of a first predetermined number of wavelet functions, and wherein each pulse train of the magnetic resonance pulse trains is defined by a second predetermined number of discrete points in time.

3. A method according to claim 1, wherein a spectrum of excitation frequencies covers frequencies of zero and integer multiples of a frequency interval.

4. A method according to claim 3, wherein the frequency interval is selected as the reciprocal value of the product of the first predetermined number and the predetermined time interval.

5. A method according to claim 1, wherein the predetermined time interval is determined whereby with the application of each pulse of the magnetic resonance pulse trains, the net magnetization of the sample is rotated by a small flip angle.

6. A Magnetic Resonance measurement apparatus employing the method of claim 1, comprising:

a) a magnetic arrangement configured to create a static magnetic field in a sample;

b) a coil configured to excite, refocus and sample a spin signal within the sample, and c) a controller operative in order to cause the magnet arrangement and the coil to perform the applying step of claim 1 as part of the method of performing magnetic resonance measurements on the sample.

7. A Magnetic Resonance measurement apparatus according to claim 6, wherein the magnet arrangement additionally comprises;

at least one magnet, of at least one of the following kinds of magnets:

a) a superconducting magnet;
b) a permanent magnet; and
c) an electromagnet.

8. A Magnetic Resonance measurement apparatus according to claim 6, wherein the magnet arrangement is a single-sided magnet arrangement.

9. A Magnetic Resonance measurement apparatus according to claim 6, wherein the controller is further operative in order to cause the magnet arrangement and coil to generate magnetic gradient fields and to produce a spatially resolved sampling of magnetic resonance measurement signals.

10. A method of operating a magnetic resonance system according to claim 1, wherein the magnetic resonance measurements are nuclear magnetic resonance (NMR) measurements.

11. A method of operating a magnetic resonance system according to claim 10, wherein the NMR measurements include magnetic resonance imaging (MRI) measurements.

12. A method of operating a magnetic resonance system according to claim 1, wherein the magnetic resonance measurements are nuclear quadrupole resonance (NQR) measurements.

13. A method of operating a magnetic resonance system according to claim 12, wherein the presence of at least one of the following materials is detected by the respective NQR measurements:

a) explosives; and
b) narcotics.

14. A method of operating a magnetic resonance system according to claim 1, wherein the magnetic resonance measurements are electron spin resonance (ESR) measurements.

15. A method of operating a magnetic resonance system according to claim 1, wherein the magnetic resonance measurements include at least one of the following:

a) bore-hole NMR measurements;
b) well-logging measurements; and
and measurements below the earth surface in porous environments comprising fluids.

* * * * *